United States Patent [19]

Schiff

[11] Patent Number: 4,522,195
[45] Date of Patent: Jun. 11, 1985

[54] APPARATUS FOR LEFT HEART ASSIST

[76] Inventor: Peter Schiff, Rte. 7, Cookeville, Tenn. 38501

[21] Appl. No.: 503,527

[22] Filed: Jun. 13, 1983

Related U.S. Application Data

[60] Division of Ser. No. 267,374, May 25, 1981, Pat. No. 4,407,271, which is a continuation-in-part of Ser. No. 172,753, Jul. 28, 1980.

[51] Int. Cl.³ .................. A61B 19/00; A61M 25/00
[52] U.S. Cl. .................................. 128/1 D; 604/96
[58] Field of Search ............ 128/1 D, 1 R; 604/96, 604/95, 104, 105

[56] References Cited

U.S. PATENT DOCUMENTS

| | | | |
|---|---|---|---|
| 3,505,987 | 4/1970 | Heilman | 128/1 D |
| 3,692,018 | 9/1972 | Goetz et al. | 128/1 D |
| 3,769,960 | 11/1973 | Robinson | 128/1 D |
| 4,015,590 | 4/1977 | Normann | 128/1 D |

*Primary Examiner*—Stephen C. Pellegrino
*Attorney, Agent, or Firm*—Louis Weinstein

[57] ABSTRACT

Apparatus for assisting the heart in the pumping of blood comprising a resilient umbrella-like member positioned within the aorta and adapted to permit the flow of blood in a normal direction and being moved to an open or expanded position to perform a pumping action and to prevent retrograde flow. The umbrella-like member may be combined for use with an intra-aortic balloon or may comprise a stand-alone pumping assembly. The umbrella-like member is preferably mounted upon a catheter for insertion in the desired location. The umbrella-like member is designed to be non-occlusive or occlusive, depending on design, when open. When used alone, operating means are provided, which means are coupled to the umbrella-like member normally maintains the umbrella in its operative, expanded position. Electromechanical control means coupled to the umbrella-like member through a control member is designed to urge the umbrella assembly to its open or closed position, depending on the direction of the control force. The umbrella assembly may also be provided with stiffener members to normally maintain the umbrella in the open position. Umbrella members of a "parachute" design and of a double conical design are disclosed. An alternative assistive assembly employs a spherical member filled with either a non-toxic gas such as, for example, air, or a saline liquid. When filled with a gas, the assembly may be inserted in a patient sitting generally in the upright position. The pumping assembly is pulled downwardly during systole and is capable of at least partially rising by itself during diastole in order to help perfuse coronaries. A drive system comprising a linear stepping motor is used to impart reciprocating movement to the control wire utilized to open and close the umbrella assembly, as well as linearly moving the umbrella assembly in a reciprocating fashion. An electronic controller operates the linear stepping motor under control of an electrocardiogram signal coupled to the controller by a three-wire circuit.

13 Claims, 21 Drawing Figures

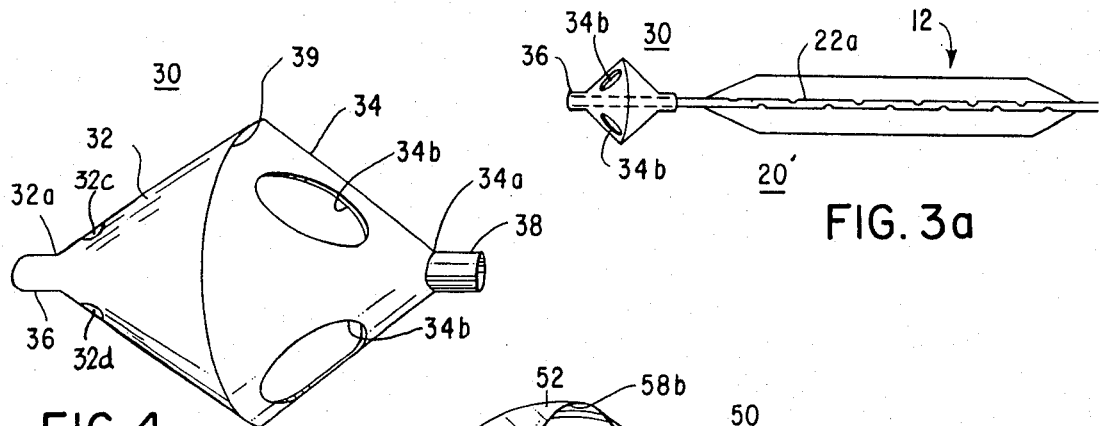
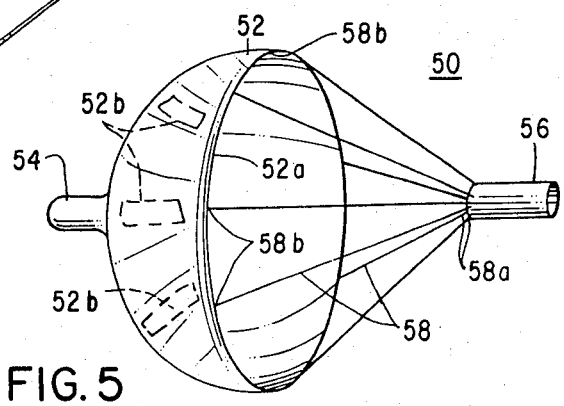
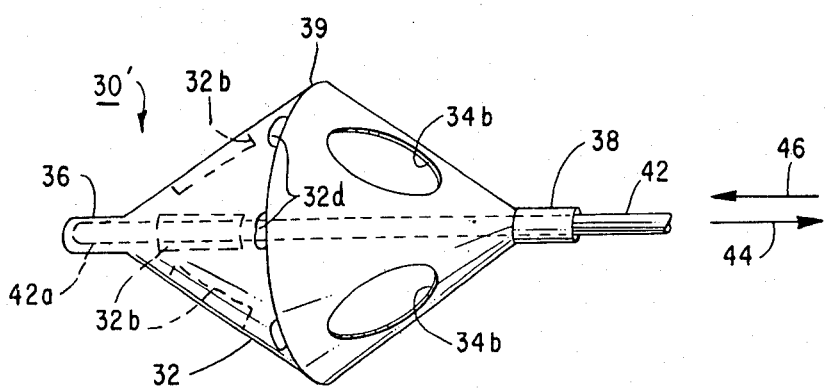
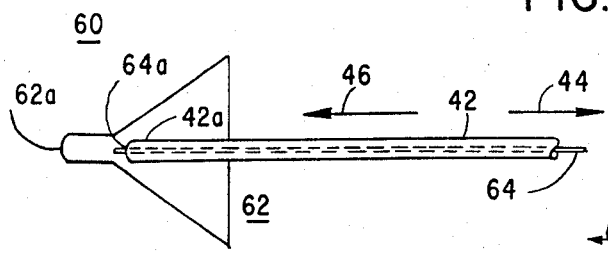
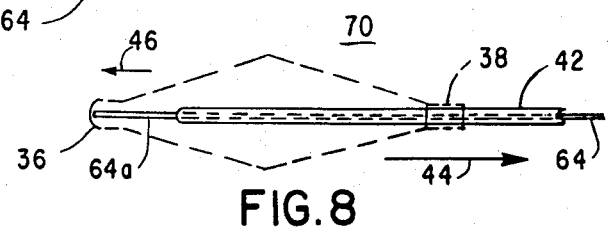

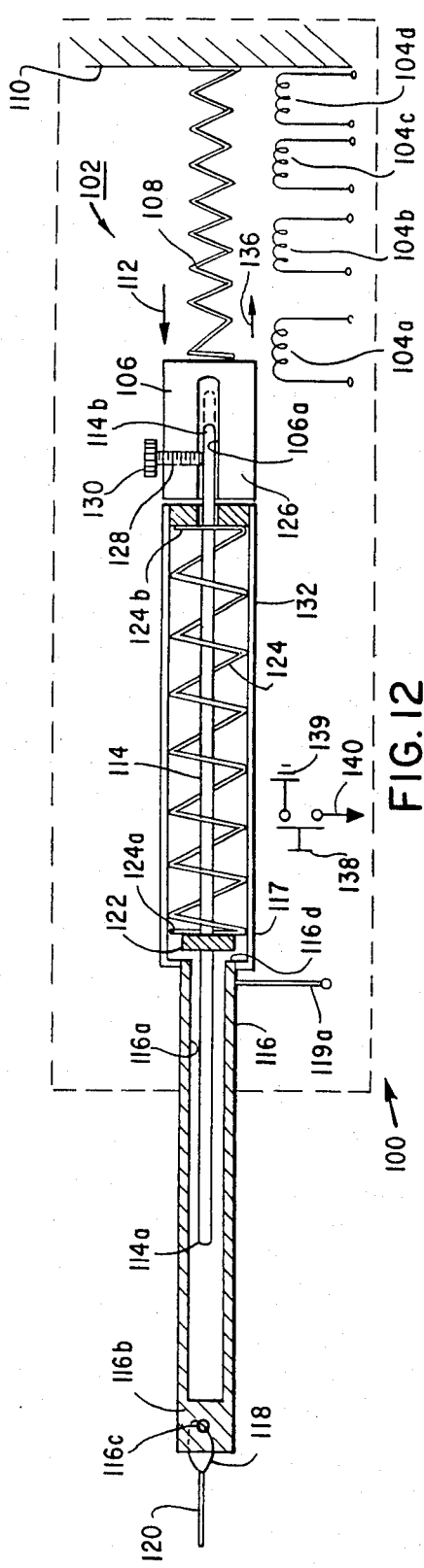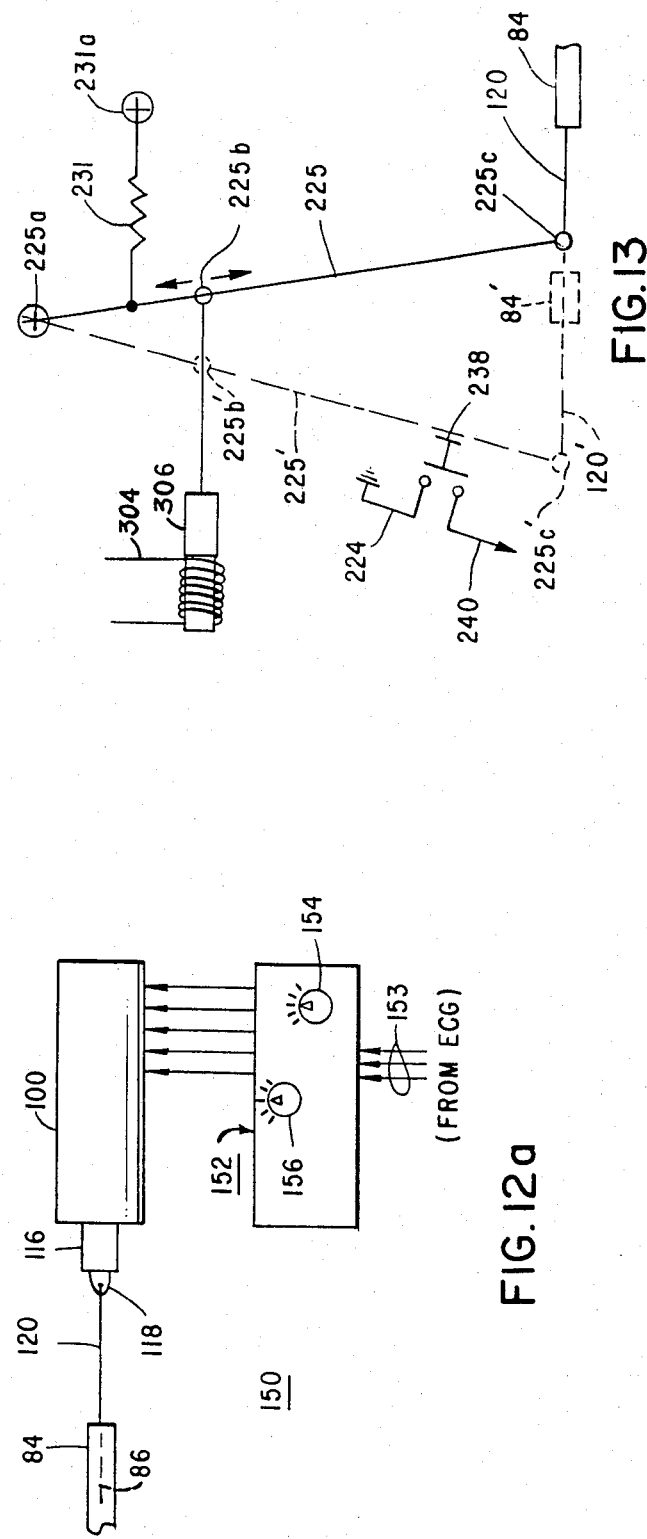

APPARATUS FOR LEFT HEART ASSIST

This application is a division of application Ser. No. 06/267,374, filed May 25, 1981, now U.S. Pat. No. 4,407,271, which is a continuation-in-part of application Ser. No. 172,753, filed July 28, 1980.

BACKGROUND OF THE INVENTION

The present invention relates to heart assist devices and more particularly to a novel, highly effective heart assist device of an umbrella-like design, and which is small and mechanically fool-proof.

Heart assist devices are presently employed to assist the pumping function of the heart either for use in patients having weakened heart conditions and/or during certain surgical procedures or treatments. Devices of this category generally in use at present comprise intra-aortic balloons, Anstadt Cups and partial bypass systems. Partial bypass systems typically comprise apparatus external to the body and coupled thereto by tubular means for assisting in the blood pumping function of the heart.

Intra-aortic balloon assist devices are comprised of a pneumatic pump system to operate an intraaortic balloon positioned in the aorta in close proximity to the aortic arch adjacent to the left ventricle. The balloon is periodically and regularly inflated and deflated in synchronism with the beating heart and is typically operated under control of the R-wave of the patient's heart. For example, the balloon is suddenly collapsed just as the left ventricle of the heart starts to eject the blood within it. This abrupt reduction of volume in the aorta, due to the collapse of the balloon, reduces the pressure therein and thereby permits the ventricle to eject the blood may readily and completely. Immediately after ejection, the balloon is then inflated, causing an increase in volume and pressure within the aorta during diastole, or the relaxation phase of the heart muscle, when the muscle is in turn perfused or supplied by oxygen in the blood at a level somewhat proportional to this diastolic pressure. Thereby, this higher pressure causes improved blood circulation, especially to the heart and also to the brain.

The work reduction of the left ventricle due to the balloon's deflation is conventionally represented by the product of the pressure reduction times the volume of blood of the ejection. This is the equivalent "potential energy" equation from physics relating to equivalent height (pressure) times weight (volume).

It is believed by the present inventor that the other energy component, namely kinetic energy, is even more relevant to improving the work reduction of the left ventricle, especially when more extensive assistance is to be provided to a failing heart with a balloon limited in volume by the small arteries of the patient. This kinetic energy is equivalent to $\frac{1}{2} \times m \times v^2$. In other words, it is proportional to the weight of the blood displaced by the balloon times the square of the velocity of the blood as it moves away from the ventricle towards the deflating balloon.

In contrast to the foregoing, retrograde blood flow coming from the aorta below the balloon and the lower extremities during and due to the deflation of the balloon will move upward and oppose the downward flow from the heart. It therefore opposes the kinetic energy work reduction to the left ventricle.

It is, therefore, important to provide a simple and yet highly effective mechanical assist device which is designed so that the retrograde flow resulting from balloon deflation as well as undesirable consequences of retrograde flow, may be eliminated or significantly reduced.

BRIEF DESCRIPTION OF THE INVENTION

The present invention is characterized by comprising an umbrella-like structure which may be employed either as a stand-alone pumping device or in conjunction with an intra-aortic balloon and which operates in a unilateral fashion to permit the free passage of blood during the ejection phase of the heart while expanding to provide assistive pumping action and also to substantially eliminate retrograde flow, as well as the undesirable consequences of retrograde flow, which occur when the intra-aortic balloon is deflated.

In an alternative embodiment, the umbrella assembly may be used to assist the pumping action of the heart as well as eliminating retrograde flow by opening or expanding during the ejection phase and being moved over a predetermined linear distance to assist the blood pumping action of the heart, and thereafter assuming the collapsed position to permit blood to pass freely from the left ventricle and along the aorta during the ejection phase, the umbrella assembly thereafter being moved to its initial starting position in order to initiate a subsequent assistive pumping action.

The umbrella assembly, in one preferred embodiment, may be comprised of a substantially hollow conical shaped member formed of a suitable lightweight plastic material having high tear strength and good flex life, such as, for example, relatively thin gauge polyurethane. The conical shaped member may be provided with stiffeners normally biasing the conical shaped member toward the open position while at the same time being sufficiently yieldable to the flow of blood about the conical shaped member to enable the conical shaped member to move towards the collapsed position allowing blood flow therearound. However, retrograde flow will cause the interior of the umbrella assembly to move from the collapsed position to the open position and thereby prevent the retrograde flow from reaching the left ventricle.

The umbrella assembly, in one alternative embodiment, has a parachute design comprised of either a conical or hemispherical shaped umbrella portion having a substantially circular-shaped outer periphery joined to a control member by slender strings coupled between the umbrella portion and the control member, which is positioned along the longitudinal axis of the umbrella member. The slender strings are arranged at uniformly spaced locations about the circular periphery of said umbrella member.

The control member may be mechanically moved over a short distance along the aorta and in the direction away from the left ventricle to open the umbrella member for assisting the heart in the pumping of blood. The umbrella member is thereafter moved in the reverse direction toward the left ventricle to be returned to its initial position, during which time the umbrella member closes. Any retrograde flow occurring at this time is prevented from opposing blood ejected from the left ventricle due to the fact that the umbrella portion expands as a result of the retrograde flow filling the interior of the umbrella portion which operates as a one-way valve. Blood ejected from the left ventricle during the ejection phase would cause the umbrella portion to collapse, enabling the blood from the left ventricle to flow along the aorta in order to supply all parts of the body with blood without resistance. The control member is again moved over the aforementioned predetermined distance to open the umbrella member and thereby assist the heart in its pumping action by urging blood to engage the interior surface of the umbrella portion and move the blood to the parts of the body served by the aorta.

The umbrella assembly, in another preferred embodiment, may comprise a hollow double conical-shaped arrangement in which the enlarged end portions of a pair of conical shaped surfaces are joined along a common diameter. One conical shaped portion has a solid continuous surface while the other conical shaped portion is provided with large openings to permit blood to flow to the interior of the hollow double conical shaped member. The apex of the conical shaped portion having the continuous surface receives the tip of a slender elongated guide member which is flexible and sufficiently resilient to follow the curvature of the aorta during insertion and movement. The guide means extends through a slender cylindrical member whose distal end is mechanically coupled and fluid tightly sealed to the apex of the hollow conical shaped portion having the aforesaid openings. The guide means is moved in a first direction away from the left ventricle over a distance preferably lying within the range of from 3 to 8 centimeters to assist the pumping of the heart during the ejection phase. The umbrella-like member is returned to its original upstream location by a combination of the biasing means provided within the control apparatus and by pushing on the cable to move the umbrella-like assembly over a substantially equal distance in the upstream direction whereby it is returned to the initial or upstream position. Retrograde blood flow would move the umbrella means to the open position, preventing retrograde flow from opposing normal flow from the left ventricle. The umbrella-like structure completely self-deflates passively during normal flow.

The umbrella assembly may also be provided with openings positioned in close proximity to the joining seam between the two conical shaped portions in order to prevent the peripheral portion of the balloon from engaging and possibly irritating the wall of the aorta.

For removal, the umbrella-like assembly may be slidably mounted upon the distal tip of the guide member and may slide off of the guide for removal and thereafter be removed from the aorta through a relatively minor surgical incision. Alternatively, the umbrella assembly may be linearly elongated to cause its wide diameter portion to be drawn toward the guide to significantly reduce the overall diameter of the umbrella assembly to facilitate its removal.

In still another design, the pumping device may be a liquid-tight sealed generally spherical shaped member which may be filled with a gas or a saline solution. With the patient sitting generally in an upright position, the connecting cable may be pulled downwardly to assist the pumping action of the heart while being adapted to rise by itself at least partially during diastole to help perfuse coronaries. The self-rising action is obtained as a result of having the patient sitting in a substantially upright position, and due to the buoyancy of the spherical member.

The present invention has a simplicity of design which yields an apparatus of extremely small size and diameter enabling the use of a very small diameter catheter and a preferred percutaneous insertion technique. In one preferred insertion arrangement, a metal needle is inserted into an artery. A plastic sleeve is positioned about the exterior of the metal needle. The needle is removed and a wire guide, typically used for cardiac catheterization, is inserted in the thin plastic sleeve in place of the needle. The plastic sleeve is now replaced by a heavier walled sleeve with a tapered point, which enlarges the puncture through the skin and into the artery. Thereupon, another thin walled sleeve is placed over the heavy walled, tapered sleeve, which is then pulled out along the wire guide. This dialator technique, which is conventional, allows for the insertion of larger diameter catheters. The small diameter catheter of the pumping device is inserted through the plastic sleeve and into the artery where it is guided therealong until it reaches the proper position within the aorta.

A drive system for the umbrella-like member may employ either an intermediate spring or clutch means to prevent an excessive pull from being exerted upon the umbrella member. A cable connects the umbrella member to an electromechanical control means which is preferably a linear stepper motor having a simplified single time delay adjustment to adjust the start of the "pull" on the cable a preselected time after the patient's R-wave or trigger signal. Additional control means may include a speed adjustment for adjusting the speed of the pull; a distance adjustment for adjusting the distance over which the cable is pulled; and on-off switch means. Compression spring means is provided for automatic return of the umbrella assembly to its start position upon deenergization of the linear stepper motor and tension spring means provides a resilient coupling between the ferromagnetic core member of the linear stepper motor and the cable. Safety switch means is provided for creating an alarm condition in the event that excessive pulling force is needed to draw the cable to the outermost position.

OBJECTS OF THE INVENTION AND BRIEF DESCRIPTION OF THE FIGURES

It is, therefore, one object of the present invention to provide a novel heart assist device for aiding the left ventricle in the pumping of blood, said device comprising an umbrella-like member for preventing retrograde flow from degrading the pumping action of an intra-aortic balloon or similar assist devices.

Still another object of the present invention is to provide a mechanical heart assist device comprising an umbrella-like member which automatically closes during systole to decrease left ventricular pressure and heart work and which opens as it is moved over a short distance to reduce left ventricular work during ejection.

Still another object of the present invention is to provide a novel intra-aortic balloon device for use in treating patients while sitting in an upright position and which is adapted to be moved during diastole in order to raise the diastolic pressure and which is automatically at least partially returned to a start position to reduce left ventricular work during systole preparatory to initiation of the next diastole phase.

Still another object of the present invention is to provide novel operating means for a left ventricle assist device for operating said device in synchronism with the rhythm of the patient's heart.

Still another object of the present invention is to provide novel mechanical operating means for controlling the operation of a left ventricle assist device where the simplicity of the design of said operating means enables use of an extremely small diameter catheter for insertion and use of the mechanical operating means and which further simplifies placement of the assist device and the control means within the patient.

The above, as well as other objects of the present invention, will become apparent when reading the accompanying description and drawings which:

FIG. 3a shows a simplified diagram of an alternative embodiment for that shown in FIG. 3.

FIG. 4 shows a perspective view of another preferred embodiment of an umbrella assembly incorporating the principles of the present invention.

FIGS. 5 and 6 are perspective views showing still further alternative embodiments of the present invention.

FIGS. 7 and 8 show simplified views of still further embodiments of the present invention and incorporating design features which facilitate removal of the umbrella assembly.

FIG. 12 shows a simplified diagram of an electromechanical control apparatus for automatically operating the umbrella assembly shown in FIG. 4 of the present invention.

FIG. 12a shows a block diagram of the electronic control means employed for operating the electromechanical apparatus of FIG. 12.

FIG. 13 is a simplified schematic diagram of an alternative apparatus for operating the umbrella assembly of FIG. 4, for example.

DETAILED DESCRIPTION OF THE INVENTION AND THE PREFERRED EMBODIMENTS THEREOF

Figure 1:
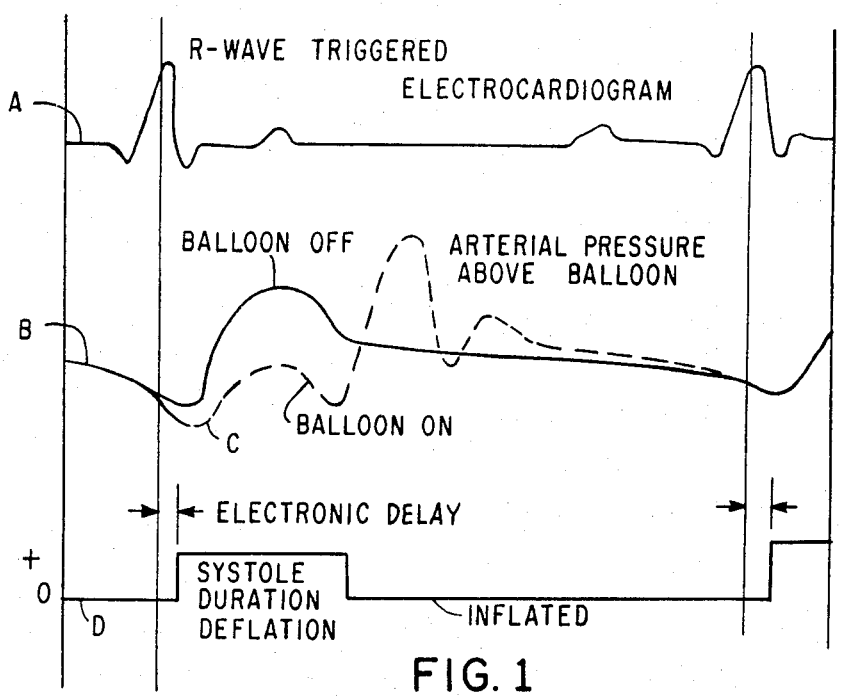
FIG. 1 shows a waveform diagram useful in explaining the manner in which state of the art mechanical heart assist devices augment the pumping of a weak heart.
Figure 2:
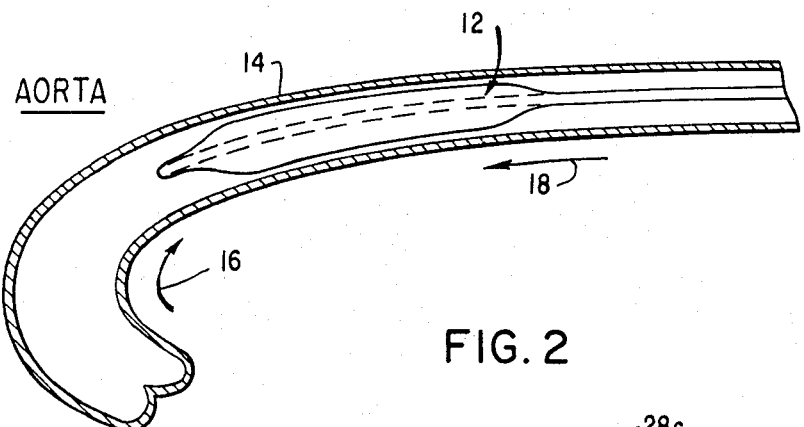
FIG. 2 shows a simplified diagram of an intra-aortic balloon positioned within the aorta and which is useful in explaining the shortcomings of the prior art.

FIG. 2 shows a conventional intra-aortic balloon 12 positioned within the aorta 14 of a patient. FIG. 1 shows a family of waveforms useful in understanding the manner in which the pumping action of a weak heart is augmented.

Waveform A is an electrocardiogram of the patient commonly referred to as the ECG signal. Waveform B represents arterial pressure within the artery 14 prior to augmentation (i.e. with balloon "off" and not being used). Waveform C represents arterial pressure as a result of augmentation (i.e. the balloon "on" and pumping). Waveform D represents the state of the electronic signal utilized to operate the pumping means (not shown) which provides positive and negative pulsatile pressure to the intra-aortic balloon 12 and which is synchronized with the ECG signal.

When the intra-aortic balloon 12 is properly positioned through either femoral artery, the balloon 12 is operated by pulsatile pressure generating means (not shown) for inflating the balloon 12 during diastole and for deflating balloon 12 during systole in order to decrease left ventricular pressure and heart work. Immediately after left ventricular ejection, the balloon 12 is again inflated to raise diastolic pressures and increase coronary perfusion. Balloon operation is adjustably triggered by the R-wave of the ECG signal. Balloon deflation is preferably electronically and pneumatically delayed by a predetermined adjustable amount so that deflation coincides with the actual left ventricular ejection.

During balloon augmentation, the onset of balloon deflation and the duration of balloon deflation are independently and selectively adjusted in order to more effectively reduce left ventricular pressure and raise diastolic pressures during balloon inflation. A more detailed description of this operation is set forth in detail in U.S. Pat. No. 4,175,264 which was issued to this inventor on Nov. 29, 1979.

The work reduction of the left ventricle due to the intra-aortic balloon 12 is commonly characterized as being a function of static blood pressure which, in turn, is equivalent to height times volume (h×v) of a representative blood column. This has been the normal way of characterizing the explanation of the work performed by the intra-aortic balloon in augmenting the pumping action of the heart. However, it is believed by this inventor that a more significant way of representing the work performed by a mechanical assist device is more appropriately expressed in the form of the kinetic energy component where kinetic energy, which is equal to $\frac{1}{2} mv^2$, may also be expressed as a function of volume times velocity$^2$, wherein volume times mass per unit volume equals total mass. As a result, it is believed that the decrease in systolic pressure does not adequately describe the improvement provided as a result of augmentation by the mechanical assist device. This novel approach will be better understood when considering the design and operation of the mechanical assist device of the present invention.

As was described hereinabove, intra-aortic balloon 12 collapses during systole, helping blood ejected from the left ventricle into the aorta to flow in the direction indicated by arrow 16. When the balloon 12 collapses, retrograde flow in the direction shown by arrow 18 is initiated as a result of balloon collapse, developing a turbulent condition with normal flow, which condition serves to oppose ejection during systole.

Figure 3:
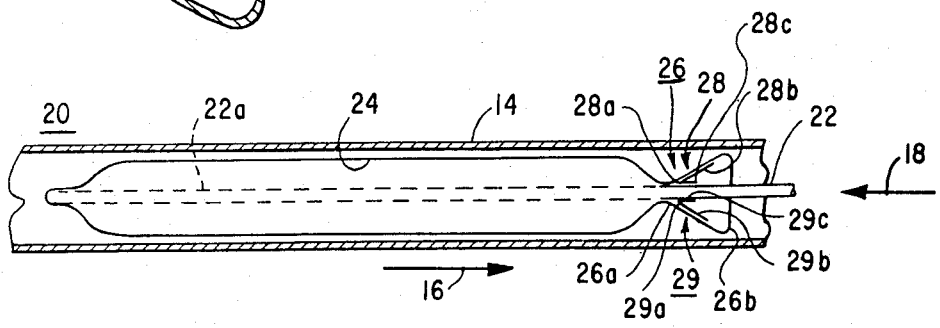
FIG. 3 shows a plan view of a novel intra-aortic balloon assembly employing the umbrella assembly of the present invention and which eliminates the disadvantages encountered when using the conventional design of FIG. 2.

FIG. 3 shows a novel intra-aortic balloon design 20 embodying the principles of the present invention in order to eliminate the harmful effects of retrograde flow.

The novel intra-aortic balloon assembly 20 of FIG. 3 comprises a hollow flexible tubular member 22 designed to introduce positive and negative pressure pulses through suitable openings (not shown) in the portion 22a of tubular member 22 which is contained within the inflatable balloon portion 24 in order to respectively inflate and deflate balloon portion 24. The intra-aortic balloon assembly 20 is positioned within the aorta 14 and is designed to operate in much the same fashion as the intra-aortic balloon 12 shown in FIG. 2. Positioned immediately adjacent to the balloon portion 24 is an umbrella assembly 26 comprised of a hollow substantially conical shaped shell 26 preferably formed of a suitable plastic material such as polyurethane having high tear strength and good flex life. The apex portion 26a of the conical shaped shell 28 is joined to the exterior surface of tube 22 by fusion, epoxy, a suitable adhesive means or any other conventional joining means or substance. The shell 26 may be provided with a plurality of equispaced stiffener members, two such stiffener members 28 and 29 being shown in FIG. 3. Each stiffener member 28, 29, is bent at its forward end 28a, 29a, to form a long leg 28b, 29b, extending along the exterior of shell 26 and a short leg 28c, 29c, extending along tube 22. The stiffeners 28, 29 tend to urge the shell 26 towards the open position when little or no pressure is applied to the exterior surface of the shell 26. Alternatively, the stiffeners 28 may be omitted and the shell 26 may be formed to have either a "natural" set or elastic memory in order to normally occupy either an "open" or a "blocking" position and thereby be more effective for the initial retrograde flow while closing only for "normal" flow. The umbrella-like structure 26 of FIG. 3 may be either of the occlusive or non-occlusive type. The example to be described, however, will be of the non-occlusive type. The operation of the novel balloon assembly of FIG. 3 is as follows:

Balloon portion 24 is deflated during systole to help blood flow in the direction shown by arrow 16. The deflated balloon portion allows blood to flow substantially unhindered in the direction shown by arrow 16. The force exerted by the blood upon the exterior surface of conical-shaped member 26 is more than sufficient to overcome the resilience of the stiffener members 28, 29, whereupon the umbrella assembly 26 "closes", i.e. collapses, to likewise permit unhindered blood flow in the direction shown by arrow 16.

Immediately after left ventricle ejection, balloon portion 24 is inflated to raise diastolic pressure and increase coronary perfusion.

Balloon portion 24 is deflated for systole whereupon the pressure differential permits retrograde flow in the direction shown by arrow 18. The stiffeners 28, 29, aided by the retrograde flow, move the umbrella assembly 26 to the open position to substantially prevent the retrograde flow from passing beyond umbrella assembly 26 toward the left ventricle. The outer diameter of the peripheral edge 26b is preferably chosen to be slightly less than the inner diameter of the aorta 14 so that the umbrella assembly 26 is operated in an non-occlusive manner. Thus, even though some retrograde flow will pass to the left of the umbrella assembly 26, the amount of retrograde flow moving to the left of the umbrella assembly 26 is relatively insignificant.

As a further alternative, cable means (not shown in FIG. 3) may be utilized to mechanically move the umbrella assembly 26 between the open and closed positions in synchronism with the ECG signal to accomplish the same result but through automatic means synchronized with the ECG signal.

FIG. 3a shows an alternative embodiment 20' of the assembly 20 shown in FIG. 3 wherein the umbrella-like structure 30, of the type shown in FIG. 4, is arranged at the distal end 36 of member 22 and the intra-aortic balloon 12 is positioned inwardly from the distal end 36 and inwardly from the umbrella-like structure 30. The operation of the embodiment of FIG. 3a is substantially the same as the embodiment of FIG. 3.

FIG. 4 shows an umbrella assembly 30 which may be used either as a stand-alone pumping device or as a substitute for the umbrella assembly 26 used in the combined balloon/umbrella assembly 20 shown in FIG. 3. The umbrella assembly 30 of FIG. 4 is comprised of first and second hollow conical-shaped portions 32 and 34. The apices 32a, 34a, of conical portions 32 and 34 are fixedly secured to the hollow cylindrical members 36 and 38 respectively. The opposite circular edges of the large ends of conical shaped members 32 and 34 are joined along a common seam 39. Conical portion 34 is provided with a plurality of equispaced substantially oval-shaped openings 34b enabling fluid to freely flow into and out of the interior of the umbrella assembly 30. The diameter of umbrella assembly 30 measured along common seam 39 is preferably equal to or less than the inner diameter of the aorta in which it is positioned in order to provide non-occlusive or occlusive operation during use as desired. Openings 32d are provided in portion 32 to prevent occlusion. Openings 32c are provided in portion 32 to allow a small amount of retrograde flow through the valve to prevent a stasis and associated blood clots within the valve.

FIG. 6 shows an umbrella assembly 30' substantially similar to the umbrella assembly 30 of FIG. 4 and is useful in explaining the manner in which the umbrella assembly 30' augments the blood pumping function. As shown therein, umbrella assembly 30' is designed to be mounted upon a slender cable 42 which extends through the hollow cylindrical members 38 and 36. The left hand end of member 36 is closed so as to limit the movement of the distal end or tip 42a of operating cable 42. During systole, cable 42 is pulled in the direction of arrow 44. Cylindrical member 38 is secured to cable 42 causing the umbrella means 30' to be pulled to the right together with cable 42. The conical shaped portion 32 may be preferably provided with stiffeners 32b (similar to stiffeners 28, 29, of FIG. 2) to stiffen the umbrella assembly 30' in the open position. By pulling cable 42 in the direction shown by arrow 44, the blood freely enters through openings 34b and fills the interior of umbrella assembly 30'. The umbrella assembly 30' is moved over a linear distance which is preferably in the range of from 3 to 8 centimeters, performing work on the blood which is a function of volume (v) times velocity squared ($v^2$), (i.e. $Vv^2$), the volume being the product of the corresponding cross-sectional area and the length of the equivalent blood column in the aorta and the linear distance over which the umbrella assembly 30' is moved. As was mentioned above, the umbrella assembly 30' is pulled at the start of systole, or slightly earlier and is thereafter moved back to its original position by moving cable 42 in the direction shown by arrow 46. The umbrella assembly 30' is adapted to collapse to permit normal flow to occur in an unimpeded fashion, the resilience of stiffener members 32b being insufficient to retain the umbrella assembly 30' in the open position during the ejection phase.

In order to prevent the seam portion 39 from engaging the interior wall of the aorta, additional openings 32c are arranged at spaced intervals along conical shaped portion 32 and in close proximity to common seam 39 to allow blood collected within the interior of the umbrella assembly to flow out of the holes 32c and strike the interior wall of the aorta at an angle to maintain the umbrella assembly 30' spaced from the interior wall of the aorta.

The umbrella design of FIG. 6 is preferably non-occlusive to prevent possible abrasion or trauma to the interior wall of the aorta. Due to the conical design of the umbrella, movement of the umbrella in the direction shown by arrow 44 will cause blood flow over the outer diameter of the cone towards the common seam 39. This flow has the tendency to keep the umbrella away from the wall of the aorta.

FIG. 5 shows another embodiment 50 of the present invention which is comprised of a hemispherical-shaped shell 52 having a hollow cylindrical shaped member 54 provided at its center. A second cylindrical shaped member 56 is joined to the lip 52a of the shell 52 by means of a plurality of slender strings 58 having their right-hand ends 58a secured to cylindrical member 56 and having their left-hand ends 58b arranged at equi-spaced intervals about lip 52a. If desired, the slender wires 58 which are preferably formed of an inert material such as a high tensile strength plastic or alternatively a fine wire encapsulated in a plastic sleeve, may also be formed of narrow plastic strips having a width several times greater than its thickness. The assembly 50 may be mounted upon a cable such as, for example, the cable 42 shown in FIG. 6 wherein the distal end or tip 42a is received within the interior of hollow cylindrical member 54 and so that the cable 42 extends through hollow cylindrical member 56 and is fixedly secured thereto at a spaced predetermined distance from the distal end or tip 42a. Hemispherical shaped shell 52 may likewise be provided with stiffener members 52b to normally urge the shell 52 toward the open position. Alternatively the material from which the shell 52 is formed may be "set" to assist the opening up of the umbrella member 52 by normally biasing the umbrella towards the open position. The operation of the embodiment 50 of FIG. 5 is substantially the same as that described in connection with the embodiment 30' of FIG. 6.

FIGS. 7 and 8 show arrangements which may be utilized to facilitate removal of an umbrella assembly when mechanical augmentation is terminated. Noting, for example, the embodiment 60 shown in FIG. 7, the umbrella member 62 has a substantially hollow conical-shaped configuration provided with a hollow portion 62a for forcefittingly receiving the distal end or tip 42a of cable 42. The forcefitted arrangement is sufficient to allow the umbrella member 62 to move with the movement of cable 42 in the directions shown by arrows 44 and 46 which movement occurs during normal operation. To facilitate the removal of the umbrella assembly, from the patient, cable 42 is not permanently attached with its tip 42a to the closed and hollow tip 62a of the umbrella. Instead, for the withdrawal and removal of the wire guide and umbrella, the umbrella slides off the tip of the wire 42a so that it has the appearance shown in FIG. 8 with a much smaller overall diameter. In use, movement of the wire and umbrella in direction 44 is rapid enough to force the blood into the convex portion of the umbrella, creating a force that will increase its outer diameter and force tip 62a on to guide 42a.

Considering the embodiments 60 and 70 of FIGS. 7 and 8, a wire 64 may be provided within the hollow interior 42a of cable 42 to separate the hollow tip 36 of umbrella member 30 from the tip 42a of cable 42. Since cylindrical member 38 is affixed to cable 42, tip 36 moves away from member 38 when wire 64 is moved in the direction of arrow 46, whereby the umbrella member 60 is moved off of tube 42 (FIG. 7) and whereby member 70 is stretched out in the axial direction (FIG. 8) causing its central portion to collapse to a very small diameter only slightly larger than the outer diameter of cable 42, facilitating removal of the entire umbrella assembly 70 from the aorta.

Figure 10:
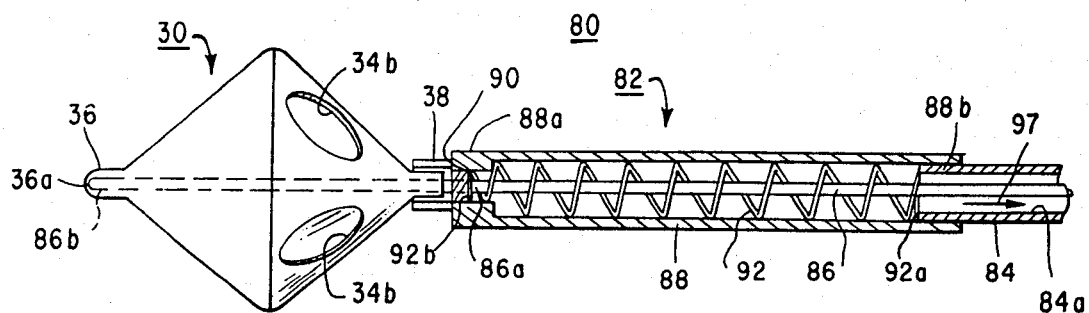
FIG. 10 shows a simplified, partially sectionalized, view of a control apparatus and which is helpful for explaining the operation thereof.

FIG. 10 shows another pumping device arrangement 80 in which a resilient member 92 is utilized within the cable assembly 82. The embodiment 80 of FIG. 10 is comprised of an umbrella assembly 30 substantially identical to that shown in FIG. 4 wherein like elements are designated by like numerals as between FIGS. 4 and 10. The cable assembly 82 of FIG. 10 is comprised of hollow tubular member 84 having its hollow interior 84a adapted to receive a reciprocally movable operating cable 86. Cable 86 extends through tubular members 84, hollow collapsible elastic sleeve 88 and a ring-shaped collar 90. Collar 90 is secured to both hollow cylindrical member 38 and cable 86 at location 86a. Cable 86 extends beyond members 38 and 90 so that its tip 86b extends into hollow tip 36 and rests against the closed end 36a thereof.

Sleeve 88 is liquid-tightly sealed at its left-hand end 88a to annular shaped member 90 and is sealed at its right-hand end 88b to hollow tubular member 84 to provide a liquid tight seal and thereby prevent blood from entering into the interior region of tubular member 84 and sleeve 88. An elongated helical spring 92 is positioned within sleeve 88 and has its right-hand end 92a bearing against the left-hand end of tubular member 84 and has its left-hand end 92b resting against the right-hand surface of annular shaped member 90. Spring 92 normally urges member 90 away from member 84.

In operation, cable 86 is moved in the direction shown by arrow 97 while tubular member 84 is held stationary, causing cable 86, members 90 and 38 and hence the entire umbrella assembly 30 to move toward the right over a distance determined by the pull exerted on cable 86. Spring 92 thus undergoes compression. When the pulling force on cable 86 is released, umbrella assembly 30 is returned "upstream" (i.e., to the left) by the collective forces exerted by cable 86 and charged compressed spring 92.

Electromechanical means 100 for operating cable 86 and hence umbrella assembly 30 is shown in detail in FIG. 12 and is comprised of a linear stepping motor 102 utilized to convert electrical signals into linear mechanical movement, said motor 102 being comprised of a plurality of coils 104a through 104d, and a cooperating ferromagnetic core 106. Although only four coils are shown in FIG. 12, it should be understood that a greater or lesser number of coils may be used wherein the number of coils employed is representative of the length of the stroke experienced by the ferromagnetic core member 106. A compression spring 108 is positioned between the right-hand surface of ferromagnetic core 106 and a stationary surface 110 for normally urging ferromagnetic core 106 in the direction shown by arrow 112.

Linear stepper motors are well known in the art and a detailed description will be omitted herein for purposes of brevity. For purposes of the present invention, however, it is sufficient to understand that the coils 104a–104d are successively energized from left to right in a sequential pattern with the total number of coils being so energized determining the distance over which the ferromagnetic core 106 is moved such that the maximum distance moved occurs when all windings are sequentially energized and a lesser stroke length is obtained by reducing the total number of windings which are sequentially energized from left to right.

Ferromagnetic core 106 is provided with a bore 106a for receiving the right-hand end of an elongated, preferably bendable but incompressible member 114. The left-hand end 114a of member 114 extends a predetermined distance into the hollow interior 116a of an elongated tubular member 116 open at its right-hand end 116d and closed at its left-hand end 116b. An eyelet 116c is provided to receive one end loop 118 of wire 120 which may either be the same wire as cable 86 shown in FIG. 10 or alternatively may have its left-hand end secured to the right-hand end of wire 86.

The flexible elongated member 114 has secured thereto a flange 122 which limits the penetration distance of member 114 into the hollow interior 116a of member 116. A helical tension spring 124 has its right-hand end 124b secured to the left-hand surface of a collar 126 adapted to be slidable along member 114. The right-hand end of sleeve 132 is secured to flange 126. Flange 126 is free to slide on rod 114. Flange 126 is not attached to core 106. Member 126 is not secured to the ferromagnetic core 106, which is also slidably mounted to elongated rod 114 in order to axially position ferromagnetic core 106 at any desired position along rod 114. A thin, flexible, collapsible sleeve 132 is attached to member 126 and covers rod 114 and tension spring 124.

The operation of the control mechanism of FIG. 12 is as follows:

When the linear stepper motor 102 is deenergized, spring 108 normally maintains ferromagnetic core 106 in its left-hand most position as shown in FIG. 12. Tension spring 124 normally urges flange 122 against the right-hand edge of member 116. When it is desired to pull the umbrella assembly (see FIG. 4, for example) a predetermined distance, typically over the range from 3 to 8 centimeters, a predetermined number of the coils 104a through 104d are energized in a sequential fashion from left to right causing ferromagnetic core 106 to move in the direction shown by arrow 136 against the force of spring 108, and causing elongated rod 114 to move in the same direction.

Rod 114 is moved to the right with collar 122 attached to it. This movement applies pressure on the left end of compression spring 124, transferring the pressure to collar 126 at the right end of spring 124. The pressure applied to collar 126 is limited to the tension in spring 124, so that collar 126 and cable 120, in turn, will only move to the right if there is no significant resistance to this movement by the umbrella assembly attached thereto. By adjustment of the position of rod 114 in the core 106, the tension on spring 124 is altered to effect the tension in the spring 124 and the pull limit that can be exerted on cable 120. The position of rod 114 relative to member 106 is set by means of the control knob 130 and threaded rod 128.

Considering FIG. 10 in conjunction with FIG. 12, wire 120 is coupled to cable 86, pulling umbrella assembly 30 to the right.

When it is desired to return the umbrella assembly 30 to its starting position, the linear stepper motor coils 104a–104d are sequentially energized in the reverse order, i.e., from right to left. Alternatively, the coils 104a–104d may simply be deenergized, allowing ferromagnetic core 106 to be urged in the direction shown by arrow 112 under the force of compression spring 108. Helical spring 124 does not exert any influence on member 116 during the return stroke.

An alarm device is provided for indicating the presence of excessive pull. Member 119 is provided with an arm 119a which is adapted to engage contact bridging member 138 to establish an electrical path between ground terminal 139 and lead 140 when engaged by member 116d. Lead 140 is coupled to an alarm such as a buzzer and/or a flasher or a lamp for creating an alarm condition in the event that member 116 has not been moved a predetermined amount to the right. If a conductive path is made between 139 and 140, it can be assumed that the pull is not excessive.

FIG. 12a shows a control arrangement 150 in which a light-weight portable, preferably battery operated, controller 152 is coupled through a three-wire circuit 153 to an ECG signals (patient) generating source (not shown for purposes of simplicity). The controller 152 is provided with an adjustable delay circuit such as a type 555 timer having settable knob 154 for setting the delay between initiation of the R-wave and energization of the linear stepper motor 102. The controller 152 is further provided with circuitry for coupling, after the preset delay, sequential signals to the linear stepper motor coils 104a–104d for example (see FIG. 12). The controller 152 may comprise electrical circuitry such as a ring counter and settable control means for setting the number of stages of the ring counter to be energized. A driver circuit is coupled to each output stage of the ring counter for coupling signals of sufficient current strength to associated ones of the windings 104a through 104d. The input to the ring counter may be an adjustable frequency oscillator.

Wire 120 is shown as being coupled to the cable 86 arranged within member 84 (note also FIG. 10).

Figure 9:
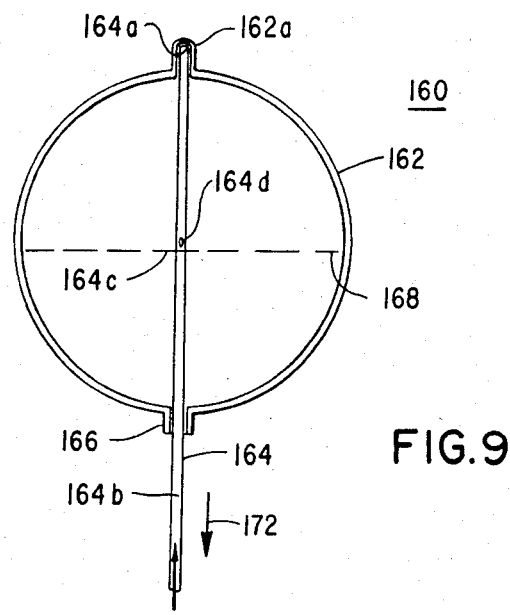
FIG. 9 shows still another embodiment of the present invention and which is especially advantageous for use in treating patients while sitting generally in an upright position.

FIG. 9 shows still another embodiment 160 of the present invention which is comprised of a hollow spherical shaped member 162 which is designed to provide non-occlusive operation and is formed of a suitable plastic material. Pull cable 164 extends through spherical shell 162 and has its tip 164a fitted within hollow tip 162a of member 162. Cable 164 also extends through cylindrical shaped member 166 and is secured thereto. Cable 164 is provided with a lumen 164b for introducing a liquid, such as a saline solution 164c, or a gas into the interior of member 162 through opening 164d along the side wall of member 164. Cable 164 may be joined to a mechanism of the type shown, for example, in FIG. 12. The assembly 160 is positioned within the aorta in a manner similar to that described hereinabove and is operated in a non-occlusive manner, i.e., it is filled to an extent so that its maximum outer diameter represented by dotted line 168, is less than the inner diameter of the aorta.

In the embodiment in which hollow spherical member 162 is at least partially filled with air, by sitting the patient being treated in an upright manner, cable 164 may be pulled in the direction shown by arrow 172 during systole and thereafter is caused to rise by itself at least partially during diastole in order to help perfuse coronaries. The embodiment 160 may or may not be spring-assisted (similar to the embodiment of FIG. 10) in accordance with the needs of the particular application. The spherical body may be at least partially collapsed when it is returned to its initial position.

Figure 11A:
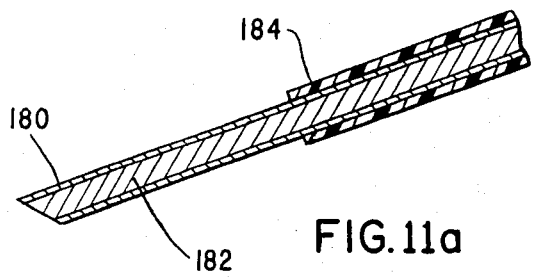
FIGS. 11a and 11b show views useful in explaining the manner in which the mechanical assist assembly in the present invention is inserted into the body.
Figure 11B:
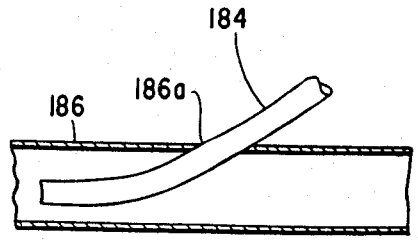

FIGS. 11a and 11b describe the manner in which an umbrella assembly of the present invention may be inserted into the aorta. A metal needle 180 is inserted into an artery together with stylet 182. When properly positioned, a plastic sleeve 184 is secured to the rear portion of needle 180. The distal end of sleeve 184 is introduced into the artery 186 (see FIG. 11b) and the stylet 182 and needle 180 are removed. The fully collapsed umbrella assembly, such as the umbrella assembly 30' shown in FIG. 6 and mounted upon cable 42, is inserted into the hollow interior of sleeve 184 and moved to the desired position in the left femoral artery, typically just below the aortic arch. The slender diameter of the simplified mechanical assist device of the present invention permits the use of a small diameter tube 184 which has an outer diameter of the order of 2 to 4 mm receiving sleeve 184 substantially eliminates the need for providing any sealing means to prevent the escape of blood from artery 186 (such as the femoral artery).

A simplified version of a solenoid actuator 200 for this cardiac assist technique is shown in FIG. 13. Here a single-coil solenoid 204 is used with a lever arm 225 pivoted at 225a to compensate for the typical solenoid's strong pulling force with a short stroke. A tempered and resilient spring steel arm 225 is free to pivot at a hinged point 225a. The solenoid 204 pulls at point 225b (through armature 206) with a short stroke. The long arm 225 converts this short stroke to a longer stroke at free end 225c, which is in turn connected to the actuator cable 120 with its sleeve 84. The solenoid has only a single coil 204 that attracts the ferromagnetic core 206 when the coil 204 is energized, causing lever 225 to move to position 225'. If excessive tension exists in lever 225 due to too much resistance in actuator rod 120, lever 225 undergoes come bending to reduce its stroke. This will result in the failure of lever 225 to move to dotted line position 225' to engage contactor 238, which in turn fails to make contact with stationary contacts 224 and 240, causing an alarm condition to be sensed by the electronic circuits in the drive assembly.

A spring 231 is attached to the lever 225 to return lever 225 to its resting position when the solenoid 204 is deactivated. The spring 231 is attached to fixed post 231a.

Figure 14:
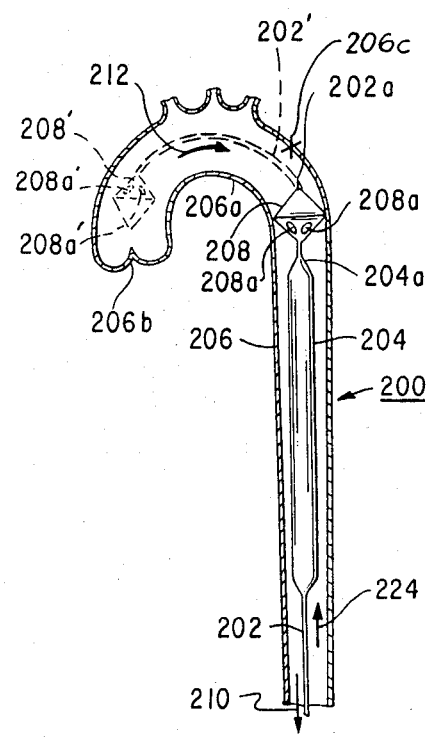
FIGS. 14 through 18 show views of still further alternative embodiments of the present invention incorporating an intra-aortic balloon and one or more umbrellas.

FIG. 14 shows an umbrella unloader assembly 200 comprised of balloon member 204 arranged along flexible tube (catheter) 202 so that its distal end 204a is positioned a spaced distance inward from the distal end 202a of tube 202 and assembly 200 is positioned within the aorta 206. Umbrella member 208 is positioned at the distal end of tubular member 206 and in the descending portion of the aortic arch 206a. Umbrella member 208 operates as a one-way valve, such that pressures created by the filling of the balloon 204 during its inflation are effectively isolated from aortic valve 206b, enabling balloon 204 to be used for aortic insufficiency. Whenever the left ventricle ejects or balloon 204 is deflated (by introducing negative pulsatile pressure in tubular member 202—see arrow 210), flow in the direction of arrow 212 simply causes umbrella member 208 to collapse allowing the free flow of fluid within the aorta and about the collapsed umbrella member 208. In this manner, the balloon 204 retains all of its left ventricular unloading qualities.

The umbrella member 208 may be positioned along tubular member 202 further apart from the distal end 204a of balloon 204 as shown in dotted fashion in FIG. 14, wherein balloon 204 remains in the original position while umbrella member 208' is arranged in the ascending arch of the aorta, closer to the aortic valve 206b, to serve as a "substitute aortic valve" which is extremely advantageous in situations where the aortic valve is seriously weakened and/or defective.

Figure 15:
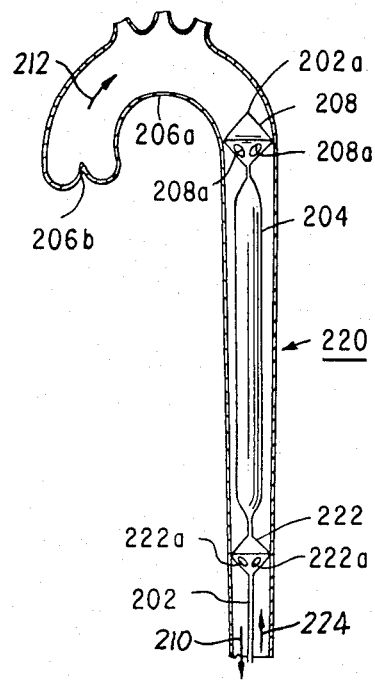

The embodiment of FIG. 14 may be further modified to provide the assembly 220 shown in FIG. 15 wherein umbrella members 208 and 222 are arranged along tubular member 202, on opposite sides of balloon 204. Both umbrella members 208 and 222 are arranged to collapse when flow occurs in the direction of arrow 212 and are arranged to open when flow occurs in the direction of arrow 224. The assembly 220 of FIG. 15 serves as a unilateral pumping assembly. When balloon 204 is deflated and/or when the left ventricle ejects, the resulting flow causes the umbrella member 208 to collapse. When balloon 204 is inflated, umbrella member 208 substantially completely isolates the pressures developed from the aortic valve and assures flow in the direction of arrow 210. Umbrella member 222 readily collapses to permit the desired flow in the proper direction.

When balloon 204 deflates, there is a normally directed blood flow downward from the direction of the left ventricle and a retrograde flow upward from the renal artery to replace the volume no longer displaced by the now collapsed balloon 204. The retrograde flow directly opposes normal flow and its flow direction and therefore significantly reduces the effectiveness of the balloon 204 in its ability to unload the left ventricle when the masses of blood (i.e. normal flow and retrograde flow) meet immediately after balloon deflation. Umbrella member 222 serves as a unilateral valve which prevents retrograde flow beyond the location of umbrella member 222. As a result, the blood that replaces the balloon volume resulting from deflation of balloon 204 must be derived from above valve means 222 and not below, thereby substantially increasing the ability of balloon 204 to unload the left ventricle. The assembly 220 has the further important advantage that the normal femoral artery pressure drops, characteristic of the deflation of balloon 204, are substantially eliminated, thereby significantly improving renal perfusion.

The inflation of umbrella members 208 and 222 due to retrograde flow imposes no impediment to normal flow. The umbrella members 208 and 222, as opposed to being rigid, are substantially limp and flexible and do not impose any hazard to balloon pumping. Even in the event that the umbrella member 208 (and/or 222) becomes occlusive during inflation, it can only push against the inner wall of the aorta 206 with a pressure equal to, and no greater than, the blood pressure itself and therefore is not expected to cause any additional trauma.

Figure 16:
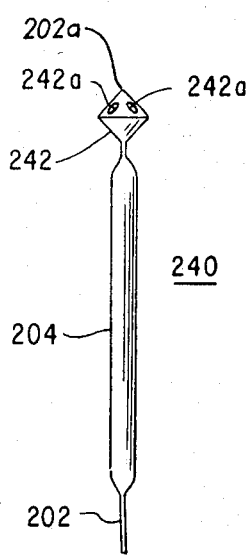

FIG. 16 shows an alternative embodiment 240 for the embodiment 200 shown in FIG. 14 wherein the umbrella member 242 is mounted at the distal end of catheter 202 and balloon 204 is spaced inwardly therefrom. However, umbrella 242 is provided with openings 242a remote from the near end of balloon 204 so as to expand and collapse in the reverse direction, thereby enabling the assembly 240 to be inserted into the body at a different location than the location at which the embodiment 200 of FIG. 14 is inserted as, for instance, when it is placed in the aorta "upside-down" from up above. For example, the assembly 240 may be inserted so that it enters into the region of the aortic arch from the ascending aorta.

Figure 17:
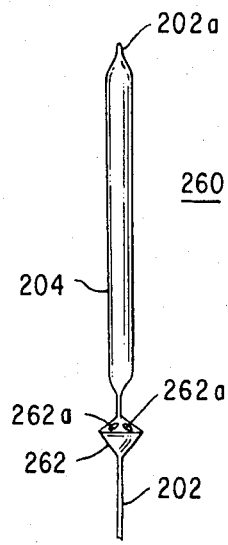

FIG. 17 shows still another alternative embodiment 260 having the balloon 204 arranged at the distal end 202a of catheter 202 and the umbrella 262 arranged a spaced distance inward from distal end 202a and balloon 204. The umbrella 262 has its openings 262a arranged so that they generally face balloon 204 enabling the assembly 260 to be inserted into the aortic arch and arranged so that the umbrella 262 and balloon 204 occupy substantially the identical positions respectively occupied by umbrella 208 and balloon 204 in FIG. 14, while catheter 202 is arranged to extend upwardly and out through the aortic arch, for example at the location 206d shown in FIG. 14.

Figure 18:
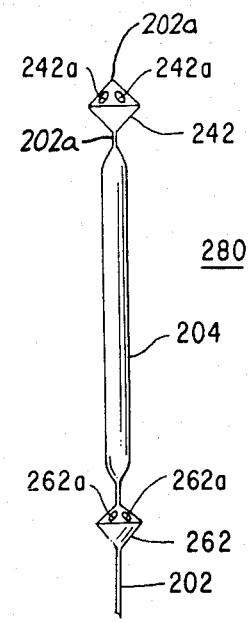

FIG. 18 shows an alternative embodiment 280 to that identified by numeral 220 in FIG. 15 and is comprised of umbrella 242 arranged at the distal end of 202a of catheter 202, balloon 204 arranged along catheter 202 a spaced distance inward from umbrella 242 and umbrella 262 arranged along catheter 202 a spaced distance inward from balloon 204. The openings 242a of umbrella 242 face away from balloon 204 while openings 262a face generally towards balloon 204, enabling the assembly 280 to be positioned within the body so that umbrella 262 occupies the position occupied by umbrella 208 (in FIG. 15), balloon 204 occupies the position occupied by balloon 204 and umbrella 242 occupies the position occupied by umbrella 222. The catheter 202, however, is arranged to extend upward and out of the aortic arch through a suitable opening provided in the wall of the aortic arch.

The embodiments of FIGS. 14-18 are not reciprocated during use as are the embodiments of FIGS. 4-6 or 10, for example.

Various alterations may be envisioned in this design of the novel assist technique presented here. For instance, the concept of mechanical assist by cable in the vascular system may be used in a reversed direction to assist primarily diastole and the perfusion of the coronaries.

A latitude of modification, change and substitution is intended in the foregoing disclosure and, in some instances, some features of the invention will be employed without a corresponding use of other features. Accordingly, it is appropriate that the appended claims be construed broadly and in a manner consistent with the spirit and scope of the invention herein.

What is claimed is:

1. Mechanical blood pumping apparatus for assisting in the pumping function of the heart comprising:
   a blood pumping element within a femoral artery of the patient to be treated;
   slender coupling means having a first end coupled to said pumping element and having a second end extending outside of the body of the patient being treated; and
   drive means connected to the second end of said coupling means for reciprocally moving said pumping element in said femoral artery between a start position and a position displaced from the start position to assist the pumping function of the heart;
   first coupling means for resiliently coupling said coupling means to said pumping element; and
   second coupling means for resiliently coupling said coupling means to said drive means.

2. The apparatus of claim 1 further comprising means for detecting the failure of said first coupling means to return to a start position upon deenergization of said drive means.

3. Apparatus for assisting the pumping function of the heart, comprising:
   elongated, flexible means having a distal end adapted to be positioned within the interior of a fluid carrying vessel within the body, and a proximate end adapted to be positioned to extend outside the body in which the distal end is inserted;
   elongated balloon means mounted along, encircling, and airtightly secured to said flexible means and having a first end thereof arranged a spaced distance inward from said distal end;
   said flexible means having means communicating with the interior of said elongated balloon means for selectively inflating and deflating said elongated balloon means;
   at least one unilateral flow control means arranged on said tubular member a spaced distance from said elongated balloon means so as to be positioned within said vessel;
   said flow control means being responsive to fluid flow in a first direction in said fluid carrying vessel to block said fluid flow and responsive to fluid flow in a direction opposite said first direction to permit fluid flow around said flow control means.

4. The apparatus of claim 3 wherein said balloon means is positioned between said distal end and said unilateral flow control means.

5. The apparatus of claim 3 wherein said unilateral flow control means is positioned between said distal end and said balloon means.

6. The apparatus of claim 3 wherein said flow control means is provided with a plurality of small openings to permit fluid flow through said unilateral flow control means when said fluid is flowing in said first direction.

7. Apparatus for assisting the pumping function of the heart, comprising:
   an elongated flexible tubular member having a distal end adapted to be positioned within the interior of a fluid carrying vessel within the human body, and a proximate end adapted to be positioned to extend outside of the body into which the distal end is inserted;
   elongated balloon means mounted along and encircling and airtightly secured to said tubular member, with a first end thereof being a spaced distance inward from said distal end;
   said tubular member having means communicating with the interior of said elongated balloon means for selectively inflating and deflating said elongated balloon means;
   first and second unilateral flow control means respectively arranged on said tubular member between said distal end and the first end of said balloon means and a predetermined distance from the end of said balloon means opposite said first end;
   said flow control means being responsive to fluid flow in a first direction in said blood carrying vessel to block said fluid flow and responsive to fluid flow in a direction opposite said first direction to permit fluid flow around said flow control means.

8. The apparatus of claim 7 wherein both of said first and second unilateral flow control means are arranged on said tubular member simultaneously to permit fluid flow in said vessel in one direction and to prevent fluid flow in said vessel in the opposite direction.

9. The apparatus of claim 7 wherein each said unilateral flow control means comprises a substantially hollow conical shaped member having its narrow end secured to said tubular member and having its free end, which defines a substantially annular periphery, adapted to move to an open position and cooperating with the interior wall of said vessel to prevent fluid flow when fluid moving in a first direction fills the interior of said conical shaped member and adapted to collapse inwardly when fluid flows in the opposite direction to allow unimpeded flow of the fluid in said vessel in said opposite direction.

10. The apparatus of claim 9 wherein said unilateral flow control means further comprises means for normally biasing said hollow conical shaped member toward said open position.

11. The apparatus of claim 7 wherein said tubular member is positioned in an arterial vessel with the distal end located in the aortic arch.

12. The apparatus of claim 7 wherein said first and second unilateral flow controls means are each comprised of a hollow flexible member surrounding said tubular member and having first and second ends secured to said tubular member;
   said flexible member having first and second conical shaped portions flaring outwardly from both said first and second ends toward one another and being joined along an annular portion intermediate portion having a diameter substantially greater than said first and second ends;
   at least one of said conical shaped portions having openings to permit fluid to enter and/or exit from the hollow interior of said hollow flexible member.

13. The apparatus of claim 12 wherein means are provided for normally biasing the hollow flexible member to the open position.

* * * * *

UNITED STATES PATENT AND TRADEMARK OFFICE
CERTIFICATE OF CORRECTION

PATENT NO. : 4,522,195

DATED : June 11, 1985

INVENTOR(S) : Peter Schiff

It is certified that error appears in the above-identified patent and that said Letters Patent is hereby corrected as shown below:

Column 1, line 37 change "may" to --more--.

Signed and Sealed this

Twenty-fourth Day of December 1985

[SEAL]

Attest:

DONALD J. QUIGG

Attesting Officer  Commissioner of Patents and Trademarks